United States Patent [19]

Collins

[11] 4,126,645
[45] Nov. 21, 1978

[54] SELECTIVE HYDROGENATION OF HIGHLY UNSATURATED HYDROCARBONS IN THE PRESENCE OF LESS UNSATURATED HYDROCARBONS

[75] Inventor: Bruce M. Collins, Stockton-on-Tees, England

[73] Assignee: Imperial Chemical Industries Limited, London, England

[21] Appl. No.: 781,415

[22] Filed: Mar. 25, 1977

[30] Foreign Application Priority Data

Apr. 6, 1976 [GB] United Kingdom ............... 13965/76

[51] Int. Cl.$^2$ ................................................ C07C 5/06
[52] U.S. Cl. ............................... 260/677 A; 260/677H
[58] Field of Search .......................... 260/677 A, 677 H

[56] References Cited

U.S. PATENT DOCUMENTS

| 2,946,829 | 7/1960 | Likins et al. ........................... 260/677 |
| 3,113,980 | 12/1963 | Robinson ............................. 260/683 |
| 3,116,342 | 12/1963 | Robinson et al. ................. 260/677 H |
| 3,308,180 | 3/1967 | Fleming ............................... 260/677 |
| 3,549,720 | 12/1970 | Wright et al. .................... 260/677 H |
| 3,635,841 | 1/1972 | Keith et al. ..................... 252/466 PT |
| 3,674,888 | 7/1972 | Derrien et al. ................. 260/677 H |

FOREIGN PATENT DOCUMENTS

| 2,240,466 | 2/1974 | Fed. Rep. of Germany. |
| 2,535,044 | 4/1976 | Fed. Rep. of Germany. |
| 1,267,794 | 3/1972 | United Kingdom. |
| 1,273,280 | 5/1972 | United Kingdom. |
| 1,397,959 | 6/1975 | United Kingdom. |

*Primary Examiner*—C. Davis
*Attorney, Agent, or Firm*—Cushman, Darby & Cushman

[57] ABSTRACT

A catalyst for selective hydrogenation of highly unsaturated hydrocarbons in the presence of less unsaturated hydrocarbons comprises palladium supported on alumina having a defined combination of micromeritic properties, the palladium being present mainly in the regions of the catalyst particles not more than 150 microns beneath their geometric surface. The alumina is made suitably by calcining pseudoböhmite at 1000°–1200° C. The catalyst has a long working life in "front-end" or "tail-end" hydrogenation.

8 Claims, No Drawings

SELECTIVE HYDROGENATION OF HIGHLY UNSATURATED HYDROCARBONS IN THE PRESENCE OF LESS UNSATURATED HYDROCARBONS

This invention relates to a catalyst and to its use in a process of selective hydrogenation of highly unsaturated hydrocarbons in the presence of less unsaturated hydrocarbons.

The manufacture of unsaturated hydrocarbons usually involves cracking saturated and/or higher hydrocarbons and produces a crude product containing hydrocarbons that are more unsaturated than the desired product but are very difficult to separate by fractionation. The commonest example is ethylene manufacture, in which acetylene is a co-product. In a similar way, formation of propylene is accompanied by $C_3H_4$ (methyl acetylene and/or allene) and the formation of butadiene by vinylacetylene. It has been found practicable industrially to remove such highly unsaturated hydrocarbons by hydrogenation, in process conditions and with a carefully formulated catalyst so that no significant hydrogenation of the desired hydrocarbon takes place. An example of such a catalytic process is described in our UK Pat. No. 916,056.

Two general types of gaseous phase selective hydrogenation processes for purifying unsaturated hydrocarbons have come into use. One, known as "front-end" hydrogenation, involves passing the crude gas from the initial cracking step, after removal of steam and condensible organic material, over a hydrogenation catalyst. Despite the large hydrogen content of such gas, very greatly in excess of the acetylenes and sufficient to hydrogenate a substantial part of the olefin present, operation with sufficient selectivity to give olefins of polymerisation quality is well established and catalyst lives of many years are obtained. In the other type, known as "tail-end" hydrogenation, the crude gas is fractionated and the resulting concentrated product streams reacted with hydrogen in slight excess over the quantity required for the highly unsaturated hydrocarbons present. The tail-end hydrogenation is less critical than front-end hydrogenation in that at the low hydrogen excess a runaway reaction is not possible; however, there is a greater tendency to deactivation of the catalyst, and consequently periodic regeneration of the catalyst is needed.

It has also been proposed to employ both front-end and tail-end selective hydrogenation in the same plant. Further, whereas the above-mentioned processes are carried out in the gaseous phase, it has been proposed to operate with the hydrocarbon in the liquid phase, especially when it contains four or more carbon atoms in the molecule.

We have now discovered a catalyst, which we believe to be a new composition of matter, by the aid of which selective hydrogenation of highly unsaturated hydrocarbons can be carried out at advantageous rates of throughput with long catalyst life between regenerations.

According to the invention a catalyst suitable for selective hydrogenation of highly unsaturated hydrocarbons comprises palladium supported on particulate alumina having a surface area in the range 5 to 50 $m^2$ $g^{-1}$, a helium density of under 5 g $cm^{-3}$, a mercury density of under 1.4 g $cm^{-3}$ and a pore volume of at least 0.4 $cm^3$ $g^{-1}$, at least 0.1 $cm^3$ $g^{-1}$ of which is pores of radius over 300 Angstrom units, the palladium being present mainly in region of the catalyst particles not more than 150 microns beneath their geometric surface.

These parameters are determined by the following methods, which are applied to samples of the catalyst each of which has been degassed at room temperature for 30 minutes at a pressure of $10^{-3}$ mm or below.

1. The density ("mercury density") of the catalyst immersed in mercury at 20° C. and 900 mm pressure, under which conditions about 15 minutes are allowed for attainment of equilibrium, is determined: this is the average density of solid containing pores not penetrated by mercury, that is, pores of radius smaller than about 6 $\times 10^4$ Angstrom units;

2. The density ("helium density") of the catalyst immersed in helium at room temperature is determined: this is the true density of the ultimate solid material. (Alternatively this density can be measured by mercury penetration of high pressure);

3. The reciprocal of this density is subtracted from the reciprocal of the density in mercury at 900 mm: the difference is equal to the total pore volume V in per gram of catalyst;

4. The surface area A per gram of the catalyst is found by the method of Brunauer, Emmett the Teller by measuring the quantity of argon adsorbed on the catalyst at 183° C.: in calculating the surface area the cross-sectional area of the argon atom is taken as 14.4 square Angstrom units. If required, the mean pore radius $\bar{r}$ can be determined by substituting the above determined volume V and area A in the formula $\bar{r} = 2V/A$ which is derived on the assumption that the pores are cylindrical and of the same size. If the volume V is expressed in cubic centimeters and the area A is expressed in square centimeters the mean radius $\bar{r}$ is in centimeters and should be multiplied by $10^8$ to give the mean radius in Angstrom units.

Within the above ranges the surface area is preferably in the range 10 to 30 $m^2$ $g^{-1}$ and the pore volume in the range 0.5 to 2.0, especially 0.5 to 1.5 $cm^3$ $g^{-1}$.

The pore volume distribution appears to be of importance in order to obtain high catalytic activity and stability. In particular, the pore volume in pores of radius over 177 Angstrom units is preferably at least as great as that in pores of radius at and below that level. It follows that the pore volume in pores of radius over 135 Angstrom units is much greater than that in pores of radius at and below that level, and thus that the catalyst is greatly different from the catalyst described in U.S. Pat. No. 2,946,829. More preferably the pore volume is predominantly (to the extent of at least 0.4 $cm^3$ $g^{-1}$) in pores of radius over 316 Angstrom units. It appears that little of the pore volume, for example less than 5%, need be in pores of radius over 3160 Angstrom units, and less than 10% in pores of radius over 1770 Angstrom units.

The palladium content (calculated as the metal) of the palladium-containing part of the catalyst particles may be suitably within the range 0.01 to 2.0, preferably in the range of 0.1 to 1.0% by weight. The catalyst may contain auxiliary materials such as other metals (for example copper, silver or gold) and oxides such as those of zinc or vanadium, but it is an advantage of the invention that such materials are not normally required.

The above-mentioned palladium contents represent the average for the regions of the catalyst particles where the palladium content is more than 0.005% by weight. The 150 micron limit of penetration of palladium is an average for any given catalyst particle. The maximum depth is under 300 especially under 225 microns. Preferably the depth of penetration in any particle is less than 90 microns on average, with a maximum of 180, more preferably 135 microns.

The specified alumina likewise can constitute the whole of the catalyst pieces or can be present as a coating (secondary catalyst support) on another material (primary catalyst support). The primary support should be one that will not cause undesirable reaction of the hydrocarbons or else should be coated thickly and coherently enough to prevent access by the hydrocarbons. Preferably the palladium is present only in the specified alumina.

The alumina support very suitably is the product of calcining a pseudobohmite alumina. Whichever alumina is used as starting material for calcination to the specified micromeritic properties, the calcination temperature is preferably at not over 1300° C. and preferably under 1250° C., for example 1000°–1200° C. In order to control the rate of sintering of the alumina, it may contain a fractional percentage, for example 0.05 to 0.5% by weight, of alkali metal oxide calculated as $Na_2O$.

The alumina support may contain a minor proportion, for example 1–10% by weight, of a divalent difficulty reducible oxide chemically combined with it as an aluminate spinel.

The catalyst conveniently is of the fixed-bed type, that is, in the form of shaped pieces whose largest dimension is in the range 2–12 mm and whose shortest dimension is at least one-third of their largest dimension. Cylindrical compressed pellets or extrusions or approximate spheres are very suitable. Wet-shaped pieces such as extrusions or granules are especially preferred because they can be cheaply made and have fully acceptable strength when the shaping operation is applied to a pseudobohmite starting material. A useful alternative catalyst is in the form of a honeycomb, the specified alumina forming the whole of the honeycomb or, more preferably, a coating on the surface of a honeycomb made of a material chosen for its mechanical properties.

The invention provides a method of making the catalyst by depositing palladium on the specified alumina. This may be effected by a dry procedure, such as sputtering, but is preferably effected by a wet process, in which a solution of a palladium compound, for example the chloride or nitrate is applied to the alumina in the form of shaped pieces by, for example, dipping or spraying. Spraying is preferred in order to obtain more reliably the desired uptake of palladium. Penetration of palladium can be controlled by suitable adjustment of the acidity of the solution, the acidity level being dependent on the alkali-content of the alumina. If desired the deposition of the palladium can be aided by a precipitant such as a slow-acting alkali (for example urea) or a reducing agent. Control of penetration is, of course, especially important if the specified alumina is present as a secondary support on a primary support made of a different material.

Since the specified alumina is not available as a commercial product, the invention provides combination methods in which the deposition of palladium is preceded by the following step or steps:

a. calcining shaped pieces of a theta or delta or pseudogamma or pseudobohmite alumina to give the specified alumina;

b. (preparatory to a) shaping pseudobohmite alumina by, for example, wet-granulation, extrusion (these are preferred), wet or dry compression-pelleting or applying to a shaped primary support; and c. (preparatory to b) producing pseudobohmite alumina by reacting an aluminium salt such as the nitrate or chloride or sulphate with an alkaline precipitant or an alkali metal aluminate with an acid such as carbon dioxide or nitric or sulphuric or hydrochloric acid, or hydrolysing an aluminium alkoxide or alkyl; the conditions for producing pseudobohmite by such reactions have been published.

After application of the palladium content to the shaped pieces, they are drained. They may be dried at a temperature in the range 25° C. to 150° C., conveniently at about 100° C., and may, without or with a distinct drying step, be heated to decompose the palladium compound, suitably at a temperature up to 500° C., especially in the range 150° C. to 450° C. The pieces may be treated with hydrogen to complete reduction to palladium metal for example during the heating step just mentioned and/or during an additional heating step (in which the temperature should be in the range 25° C. to 450° C.) after the first heating step but before use. If there is no preliminary reduction step, reduction takes place under the reducing conditions in the selective hydrogenation process. If the catalyst is reduced before use it may be stored under an inert atmosphere but should preferably not be kept for prolonged periods in hydrogen.

The invention provides also a process for hydrogenation of unsaturated compounds using the defined catalyst, especially for selective hydrogenation of highly unsaturated hydrocarbons in the presence of less unsaturated hydrocarbons.

When the process is a "front-end" hydrogenation the temperature is suitably up to 250° C., for example 60°–150° C.; the pressure is suitably in the range 1–70 ata, for example 8–40 ata; and the space velocity is suitably in the range 100–20000, for example 5000–15000 $hour^{-1}$, that is, liters per liter of catalyst-filled space per hour, calculated for 20° C., 1 ata pressure. The volume percentage composition of the gas fed to the catalyst is suitably as follows for a process producing ethylene and/or propylene as main products:

ethylene or propylene: 10–45
propylene or ethylene: up to 20 (when both are present)
higher hydrocarbons up to 2
acetylene and/or $C_3H_4$: 0.01 to 2
hydrogen: 5–40
unreactive gases (alkanes, nitrogen): balance For long catalyst life without regeneration the hydrogen content is preferably at least 5 times by volume as much as the content of acetylene and $C_3H_4$.

When the process is a tail-end hydrogenation the temperature is suitably in the range 40°–150° C.; the pressure is suitably in the range 1–70 ata, for example 8–40 ata; and the space velocity is suitably in the range 500–7000 $hour^{-1}$, that is, liters of gas per liter of catalyst-filled space per hour. The hydrogen content should be at least sufficient to hydrogenate to mono-olefin all the highly unsaturated hydrocarbons present and is preferably 1.5–3.0 times that content for acetylene and 1.1–3.0 times that content for $C_3H_4$. The life of the catalyst between regenerations is longer the higher the hydrogen content of the gas, but this advantage is counter-balanced by the expense of separating and recycling greater quantities of saturated hydrocarbon. The gas passed over the catalyst typically contains up to about 6% (for example 0.1 to 3.0%) of highly unsaturated hydrocarbons and at least 50%, commonly over 95% of the desired mono-olefin or conjugated diolefin.

When the process is a tail-end liquid-phase selective hydrogenation the temperature is typically 0°–50° C., the pressure up to about 50 ata. and the space velocity typically 5–40 kg. per hour per liter of catalyst-filled space. The liquid hydrocarbon suitably trickles downwards over the catalyst in a substantially stationary hydrogen atmosphere.

Whichever type of hydrogenation is used, it appears to be advantageous to have present a small quantity of carbon monoxide. In a front-end hydrogenation the proportion of carbon monoxide is suitably 0.03 to 3.0% v/v of the total gas mixture. Such a content commonly enters in as a by-product of the initial cracking reaction.

In a tail-end hydrogenation the proportion is suitably in the range 4.0 to 500 ppm v/v; it may be added deliberately if fractionation of the crude gas has removed it or left too little of it.

EXAMPLE 1

Preparation of catalysts A and B:

A quantity of alumina granules sold under the name "Pechiney Saint-Gobain SCS-79" was calcined at 1000°–1050° for 36 hours. The calcined granules were impregnated by dipping in an aqueous solution containing 0.77 g of palladium chloride per liter and sufficient hydrochloric acid to give a pH of 2.1. They were then dried at 450° C. for 6 hours. The loading of palladium on the granules was 0.044% by weight overall. Since the palladium penetration was 120 microns on average in each granule and the volume-averaged mean diameter of the granules was 0.31 cm, it follows that the palladium content in the palladium-containing region was 0.20%. The micromeritic properties of the finished catalyst, referred to as "catalyst A", are listed in Table 1. (Note: SCS-79 is a pseudoböhmite).

A control catalyst was prepared from an alumina trihydrate supplied by the British Aluminium Company by dehydrating, pelleting by compression to 3.6 × 5.4 mm squat cylinders and calcining at 1065° C. for 6 hours. The pellets were impregnated by dipping in an aqueous solution containing 3.1 g of palladium nitrate per liter, which had been acidified with nitric acid, and were then calcined at 450° C. for 6 hours. The overall palladium loading was 0.03% w/w and the average penetration 310 microns. The palladium content in the palladium-containing region is therefore 0.088%. The micromeritic properties of this material, "Catalyst B" are listed in Table 1.

TABLE 1

| | Catalyst A | Catalyst B |
|---|---|---|
| Total surface area ($m^2 g^{-1}$) | 34 | 22 |
| Helium density (g $cm^{-3}$) | 3.67 | 3.47 |
| Mercury density (g $cm^{-3}$) | 1.17 | 1.52 |
| Pore volume ($cm^3 g^{-1}$) | 0.58 | 0.37 |
| Mean pore radius (cm × $10^{-8}$) | 343 | 336 |
| Total sodium as $Na_2O$ (% w/w) | 0.06 | 0.37 |

TABLE 1-continued

Pore volume distribution

| radius, A | $cm^3 g^{-1}$ A | B |
|---|---|---|
| 0–100 | 0.068 | 0.053 |
| 100–177 | 0.175 | 0.043 |
| 177–316 | 0.19 | 0.059 |
| 316–562 | 0.088 | 0.059 |
| 562–100 | 0.02 | 0.043 |

Test of catalysts A and B in "tail-end" conditions

Catalysts A and B were charged to a side-stream reactor of an ethylene production plant and subjected to a life test for the hydrogenation of acetylene in a $C_2$ stream.

The test conditions were as follows:

| pressure | 200 psig |
|---|---|
| space velocity | 2000 hours$^{-1}$ |
| catalyst volume | 1800 ml |
| representative gas composition v/v: | 15% ethane |
| | 0.8% acetylene |
| | 1.6% hydrogen stream (800 ppm CO) |
| | balance ethylene |

The acetylene content of the inlet gas varied between 0.6 and 1.0% and the hydrogen stream, which was metered in separately from the other gases, was adjusted frequently to maintain a hydrogen/acetylene volume ratio close to 2.0. The catalyst temperature was adjusted to give the minimum attainable level of acetylene in the gas leaving the reactor and was generally in the range 50°–80° C. at the inlet of the bed.

The acetylene content of the reacted gas was measured at intervals. Initially it was extremely low but rose slowly as follows:

| Catalyst A | | | | | | |
|---|---|---|---|---|---|---|
| days on line | 4 | 25 | 40 | 49 | 63 | 67 |
| $C_2H_2$ (ppm v/v) | 0.007 | 0.03 | 0.04 | 0.2 | 0.8 | 1.0 |
| Catalyst B | | | | | | |
| days on line | 4 | 12 | 13 | 14 | | |
| $C_2H_2$ (ppm v/v) | 0.02 | 0.3 | 0.5 | 2.0 | | |

Since 1 ppm is commonly the maximum acceptable acetylene content, the lifetimes were evidently 66 days for a catalyst A, a catalyst according to the invention and 13 days for catalyst B, the control.

EXAMPLE 2

Preparation of catalysts C and D

Catalysts C and D were prepared from alumina granules sold as "Pechiney Saint Gobain SCM 250". For catalyst C the granules were calcined at 1050° C. for 6 hours. A 1770 g sample of the calcined granules was impregnated by spraying with 870 ml of an aqueous solution containing 1.18 g of palladium chloride and sufficient hydrochloric acid to give a pH of 2.6. The volume of solution was 90% of what was necessary to saturate the granules, and it was applied over one hour, keeping the granules continuously in motion in a rotating inclined vessel. The granules were then dried at 450° C.

For catalyst D the granules were calcined at 1070° C. for 6 hours. They were impregnated in the same manner as catalyst C except that the solution pH was 1.6–1.8, in order to distribute the palladium in a deeper layer than in catalyst C. The micromeritic properties and composition of catalysts C and D are listed in Table 2. (Note: SCM250 is a pseudoböhmite)

TABLE 2

|  | Catalyst C | Catalyst D |
|---|---|---|
| Total surface area ($m^2 g^{-1}$) | 30 | 28 |
| Helium density (g $cm^{-3}$) | 3.56 | 3.79 |
| Mercury density (g $cm^{-3}$) | 1.19 | 1.20 |
| Pore volume ($cm^3 g^{-1}$) | 0.56 | 0.57 |
| Mean pore radius (cm × $10^{-8}$) | 373 | 407 |
| Overall Pd content (% $^w/w$) | 0.038 | 0.035 |
| Penetration of Pd (microns) | 100 | 510 |
| Mean granule diameter (volume average) (cm) | 0.42 | 0.42 |
| Concentration in Pd-containing layer (% $^w/w$) | 0.28 | 0.06 |
| Total sodium as $Na_2O$ (% $^w/w$) | 0.05 | 0.06 |
| Pore volume distribution | | |

| radius, A | $cm^3 g^{-1}$ | |
|---|---|---|
|  | C | D |
| 0–100 | 0.041 | 0.113 |
| 100–177 | 0.110 | 0.162 |
| 177–316 | 0.127 | 0.091 |
| 316–562 | 0.097 | 0.048 |
| 562–1000 | 0.048 | 0.030 |
| 1000–3160 | 0.03 | 0.03 |

Test of catalysts C and D in "tail-end" conditions

These test conditions were similar to those in Example 1 except for the quantities of the hydrogen stream (800 ppm CO) used.

For the first three days the ratio of hydrogen to acetylene was maintained at approximately 3.0 and the catalyst temperature at between 100° C. and 140° C. This ensured that the palladium compounds were fully reduced and that reaction was stabilised before significant deposition of polymer and char took place. (These three days were not counted when reckoning the life of the catalysts). The ratio of hydrogen to acetylene was then decreased to approximately 1.5 and the hydrogen stream flow adjusted frequently to maintain this ratio. This ratio is lower than is normal in commercial practice, but was chosen in order to shorten the test period. The catalyst temperature was adjusted to maintain the minimum attainable acetylene content in the gas leaving the converter. This outlet acetylene content gradually rose as follows:

| Catalyst C | | | | | | |
|---|---|---|---|---|---|---|
| days at 1.5 ratio | 9 | 14 | 15 | 19 | 22 | 23 |
| $C_2H_2$ (ppm $^v/v$) | <0.01 | <0.01 | 0.02 | 1.4 | 3.7 | 5.0 |
| Catalyst D | | | | | | |
| days at 1.5 ratio | 2 | 3 | 5 | | | |
| $C_2H_2$ (ppm $^v/v$) | 0.03 | 0.13 | 5.0 | | | |

Taking 1 ppm as the maximum acceptable acetylene content, the lifetimes were evidently 18 days for catalyst C, a catalyst according to the invention, and 4 days for catalyst D.

EXAMPLE 3

Preparation of catalysts E and F

Catalyst E was prepared from pseudobohmite granules sold under the name "Kaiser Substrate Alumina SAS". A quantity of these granules was calcined at 1100° C. for 6 hours and allowed to cool. A 1400 g sample of the calcined granules was impregnated by spraying with an aqueous solution containing 0.93 g of palladium chloride and sufficient hydrochloric acid to give a pH of approximately 2.5. The impregnation technique was as described in Example 2. The granules were then dried at 450° C. for 6 hours.

Catalyst F was prepared from the alumina trihydrate supplied by the British Aluminium Company (as in Example 1) by dehydrating, pelleting by compression to 3.5 mm × 3.5 mm cylinders and calcining at 1080° C. for 10 hours. The calcined pellets were impregnated by spraying with an aqueous solution of palladium nitrate acidified with nitric acid. After impregnation the pellets were dried. The micromeritic properties and composition of catalysts E and F are listed in Table 3.

TABLE 3

|  | Catalyst E | Catalyst F |
|---|---|---|
| Total surface area ($m^2 g^{-1}$) | 19 | 16 |
| Helium density (g $cm^{-3}$) | 3.20 | 3.38 |
| Mercury density (g $cm^{-3}$) | 1.09 | 1.64 |
| Pore volume ($cm^3 g^{-1}$) | 0.605 | 0.314 |
| Mean pore radius (cm × $10^{-8}$) | 637 | 392 |
| Overall Pd content (% $^w/w$) | 0.034 | 0.03 |
| Penetration of Pd (microns) | 64 | 40 |
| Mean granule diameter (volume average) (cm) | 0.256 | — |
| Concentration in Pd-containing layer (% $^w/w$) | 0.24 | 0.45 |
| Total sodium as $Na_2O$ (% $^w/w$) | 0.08 | 0.50 |
| Pore volume distribution | | |

| radius, A | $cm^3 g^{-1}$ | |
|---|---|---|
|  | E | F |
| 0–100 | 0.005 | 0.028 |
| 100–177 | 0.022 | 0.039 |
| 177–316 | 0.040 | 0.042 |
| 316–562 | 0.071 | 0.073 |
| 562–1000 | 0.193 | 0.077 |
| 1000–1770 | 0.258 | 0.029 |
| 1770–3160 | 0.047 | 0.018 |
| over 3160 | 0.002 | 0.040 |

Test of catalysts E and F in "front-end" conditions

Catalyst E and F were tested in conditions designed to show their activity and selectivity in "front-end" hydrogenation of highly unsaturated components of olefin streams. Although conducted at atmospheric pressure, the test gives a reliable guide to performance in an industrial plant.

The catalyst bed was 2.4 cm in diameter and 5 cm deep (volume 15 ml) with an axial thermocouple sheath. The gases were preheated before reaching the catalyst and the reactor was a double-walled Dewar-type vessel so that heat losses were minimised and a correct temperature profile could be maintained within the catalyst bed. The catalysts were reduced in situ at 200° C. for an hour in a flow of 100 l $h^{-1}$ of 23% hydrogen in nitrogen. The two inlet gas compositions used, in order to simulate the two beds of an industrial reactor having a cooling stage between the beds, are set out in Table 4.

TABLE 4

| Composition (% $^v/v$) | First Bed Conditions | Second Bed Conditions |
|---|---|---|
| Acetylene | 0.30 | 0.015 |
| Methylacetylene | 0.18 | 0.036 |
| Propadiene | 0.18 | 0.072 |
| Hydrogen | 15 | 15 |
| Ethylene | 35 | 35 |
| Nitrogen | 50 | 50 |
| Carbon monoxide | 0.10 | 0.10 |

(The nitrogen simulates the inert alkanes normally present.) The volume hourly space velocity of the mixed gases was 10000 $hour^{-1}$, calculated to room temperature. The composition of the reacted gas was measured over a range at catalyst temperature from 40° to 120° C.

Catalyst performance can be usefully measured by comparing the degree of removal of the highly unsaturated components at a given degree of undesired saturation of the product olefin. In these runs the exit levels of acetylene, methylacetylene and allene were measured for various amounts of ethane produced. The measured results, given in Table 5, show that catalyst E, according to the invention, is far more selective than catalyst F, the control. It can also be seen that, for the desired reactions, catalyst E is equal in activity to catalyst F at similar or lower temperatures, that is, the improvement in selectivity of catalyst E is not gained at the expense of activity.

TABLE 5

| Exit concentrations in ppm by volume | First bed conditions | | Second bed conditions | |
|---|---|---|---|---|
| | Catalyst E | Catalyst F | Catalyst E | Catalyst F |
| i) For 100 ppm ethane formed | | | | |
| acetylene | 130 | 650 | <1 | 8 |
| methylacetylene | 600 | 1100 | 17 | 140 |
| allene | 1500 | 1600 | 500 | 600 |
| mean catalyst temp (° C) | 82 | 78 | 62 | 65 |
| ii) For 500 ppm ethane formed | | | | |
| acetylene | 24 | 140 | <1 | 1.8 |
| methylacetylene | 190 | 250 | 1.2 | 4.8 |
| allene | 1200 | 1300 | 300 | 520 |
| mean catalyst temp (° C) | 86 | 84 | 70 | 86 |
| iii) For 2000 ppm ethane formed | | | | |
| acetylene | <1 | 40 | <1 | 0.9 |
| methylacetylene | 6 | 70 | <1 | 19 |
| allene | 480 | 580 | 170 | 300 |
| mean catalyst temp (° C) | 95 | 103 | 74 | 117 |

Test of catalyst E in "tail-end" conditions

Catalyst E was tested in the conditions described in Example 2. The acetylene content increased gradually as follows:

| days on line | 10 | 21 | 32 | 35 | 37 | 38 |
|---|---|---|---|---|---|---|
| $C_2H_2$ (ppm v/v) | under 0.01 | under 0.01 | 0.04 | 0.13 | 1.0 | 4.0 |

It is evident that catalyst E has a useful lifetime of 37 days in these conditions and is thus better than catalyst C.

I claim:

1. A process of selective hydrogenation of highly unsaturated hydrocarbons in the presence of less unsaturated hydrocarbons characterised by the use of a catalyst which comprises palladium supported on particulate alumina having a surface area in the range 5 to 50 $m^2 g^{-1}$, a helium density of under 5 g $cm^{-3}$, a mercury density of under 1.4 g $cm^{-3}$ and a pore volume of at least 0.4 $cm^3 g^{-1}$, at least 0.1 $cm^3 g^{-1}$ of which is in pores of radius over 300 Angstrom units, the palladium being present mainly in the region of the catalyst particles not more than 150 microns beneath their geometric surface.

2. A process according to claim 1 which is a "front-end" hydrogenation and is operated at 60°–150° C., a pressure in the range 8–40 atm.abs., a space velocity 5000–15000 $hour^{-1}$ for treating a gas mixture having the volume percentage composition:

(a) an olefin component selected from the group consisting of

| ethylene | 10–45, |
|---|---|
| propylene | 10–45, |
| ethylene | 10–45 and up to 20 propylene, and |
| propylene | 10–45 and up to 20 ethylene; | b) higher hydrocarbons up to 2;
c) acetylene and/or $C_3H_4$ 0.01 to 2;
d) hydrogen 5–40; and the balance being unreactive gases.

3. A process according to claim 1 which is a "tail end" hydrogenation and is operated at 40°–150° C., a pressure in the range 8–40 atm. abs., a space velocity in the range 500–7000 $hour^{-1}$ for treating a gas mixture having the volume percentage composition:

| desired mono-olefin or conjugated diolefin | over 95; |
|---|---|
| highly unsaturated hydrocarbon | 0.1 to 3.0; | and in which the hydrogen content is up to 3 times that which is sufficient to hydrogenate said highly unsaturated hydrocarbon to mono-olefin.

4. A process according to claim 1 in which the pore volume is in the range 0.5 to 1.5 $cm^3 g^{-1}$.

5. A process according to claim 1 in which the pore volume is predominantly in pores of radius between 316 and 1770 Angstrom units.

6. A process according to claim 1 in which the palladium content of the palladium-containing part of the catalyst particles is in the range 0.1 to 1.0% by weight.

7. A process according to claim 1 in which the depth of palladium penetration is less than 90 microns on average.

8. A process according to claim 1 in which the alumina is the product of calcining a pseudoböhmite.

* * * * *